United States Patent [19]

Delgoffe et al.

[11] Patent Number: 4,618,493
[45] Date of Patent: Oct. 21, 1986

[54] TEMPERATURE SENSITIVE STRAINS OF BOVINE VIRAL DIARRHOEA VIRUS, PREPARATION THEREOF AND VACCINES CONTAINING THEM

[75] Inventors: Jean-Claude Delgoffe, Bierges; Michèle Lobmann, Rosieres; Nathan Zygraich, Brussels, all of Belgium

[73] Assignee: SmithKline-RIT, Belgium

[21] Appl. No.: 434,155

[22] Filed: Oct. 13, 1982

[51] Int. Cl.$^4$ .................... A61K 39/12; C12N 7/06
[52] U.S. Cl. ........................... 424/89; 435/238
[58] Field of Search .................... 424/89; 435/238

[56] References Cited

U.S. PATENT DOCUMENTS

| | | | |
|---|---|---|---|
| 3,052,606 | 9/1962 | Gierer et al. | 435/172 |
| 3,629,413 | 12/1971 | Shechmeister et al. | 435/238 |
| 3,897,549 | 7/1975 | Zygraich et al. | 424/89 |
| 3,907,986 | 9/1975 | Zygraich et al. | |
| 3,927,208 | 12/1975 | Zygraich et al. | |
| 3,962,424 | 6/1976 | Zygraich et al. | |
| 4,053,583 | 10/1977 | Gits et al. | 424/90 |

OTHER PUBLICATIONS

Coria et al., Am. J. Vet. Res. 42(4): 647–649, 1981.
Sandri–Goldin et al., J. Virol. 38:41–49 (1981).
Ray et al., J. Virol. 30:913–916 (1979).
Phillips et al., Amer. J. Vet. Res. 36:135–140 (1975).
Bittle et al., J.A.V.M.A. 163:878–879 (1973).

*Primary Examiner*—Sidney Marantz
*Assistant Examiner*—Shawn P. Foley
*Attorney, Agent, or Firm*—Edward T. Lentz; Janice E. Williams; Alan D. Lourie

[57] ABSTRACT

A live bovine viral diarrhoea (BVD) virus vaccine capable of producing immunity in bovines without causing significant side effects comprising a temperature sensitive (ts) mutant of BVD virus which is obtained by mutating a strain of BVD virus with nitrous acid. The temperature sensitive mutants show a replication ability considerably limited at the animal body temperature of 39.5° C. The vaccine may be combined with other live bovine vaccines such as respiratory virus vaccines and then administered to bovines.

17 Claims, No Drawings

TEMPERATURE SENSITIVE STRAINS OF BOVINE VIRAL DIARRHOEA VIRUS, PREPARATION THEREOF AND VACCINES CONTAINING THEM

This invention relates to modified strains of bovine viral diarrhoea (BVD) virus, to the preparation thereof and to the vaccines containing them.

Bovine viral diarrhoea disease is one of the most widespread and economically important disease of cattle. It was first recognized in the United States (OLAFSON et al., Cornell Vet. 36:205-213, 1946) when herd outbreaks of an acute, frequently fatal, rinderpestlike syndrome with ulcerations of the alimentary mucosa and diarrhoea were observed. Concurrently, similar cases with variations in degree of severity, chronicity, and sporadicity were described and named mucosal disease (RAMSEY F. K. et al., North Am. Vet. 34:629-633, 1953). For some time it was thought that several different infections existed. It was eventually concluded that the same virus was responsible for both syndromes, but this was not until after both terms had become ingrained in the literature and the term mucosal disease complex was in common usage. According to priority the disease was called bovine viral diarrhoea.

The etiologic agent of BVD is an RNA virus classified as a pestivirus of the family Togaviridae (ANDREWES C. et al., Viruses of the Vertebrates, 4th ed., London; Bailliere Tindall, 1978).

The manifestations of clinical disease in the field vary considerably. In general an incubation period of 7-11 days is followed by a mono- or di-phasic pyrexia of 39.5°-41.5° C., anorexia and diarrhoea. Sometimes, the diarrhoea progresses to the voiding of undigested food, blood flocked mucus and diphteritic strands, accompanied by violet tenesmus. Despite a concurrent polydipsia the animals become dehydrated and rapidly lose condition.

Although BVD is chiefly associated with an infection of the alimentary tract, it has been suggested that the sequence of symptoms usually begins with respiratory involvment: a serous or mucous nasal discharge later becoming purulent together with polypnoea and coughing (S. F. ROSNER, Iowa Vet. 35: 11-14, 1964). Numerous authors also reported nasal discharge progressing from the serous to the mucopurulent.

The major pathological changes associated with the disease are hyperaemia, haemorrhage, oedema, erosion and ulceration of the alimentary mucosae. Congestion of the mucous surfaces of the respiratory tract are also observed, as well as pulmonary oedema. A profound leukopenia is usually present, particularly in the early stages of the infection. Total white blood cell counts were observed to return to normal levels about 14 days after experimental inoculation (SCOTT F. W. et al., Cornell Vet. 63:536-560, 1973).

On these bases, MILLS J. H. L. et al. (Am. J. Vet. Res. 29: 1367-1375, 1968) suggested that "transmission via the respiratory route is a possible mode of spread".

Congenital immunotolerance to BVD infection has been incriminated as a potential cause of the seldom fatal disease and it is known that immunodepression induced by corticoïd treatment potentiates the virulence of artificial infection with BVD. The immunodepressed animals often succumbed to a generalized viraemia (ROHDE, G. et al., Zbl. Vet. Med. 17 B:686, 1970, and SHOPE R. E. et al., Can. J. Comp. Med. 40:355-359, 1976).

Once overt clinical signs are observed in a herd, the infection is usually well established in affected individuals and in the herd. Specific therapeutic measures are not available for treating clinical cases. If severe, they usually succumb; if mild, recovery may be expedited by antibiotics to control secondary infection.

Under ordinary farm conditions, attempting to maintain a "closed herd" has proven inadequate for preventing infection with BVD virus. Therefore preventive methods are largely based on vaccines.

There has been considerable investigation of inactivated vaccines (McCLURKIN A. W. et al., Pro. US Anim. Health Assoc. 79:114-123, 1975). As yet, these are not commercially available. Their practical usage is impaired by the lack of an adequate technology for production of acceptable dosage forms for delivery of required antigenic masses in an economically acceptable fashion.

Some commercial BVD live vaccines are known. As reported by R. M. PHILLIPS et al. (Am. J. Vet. Res 36:135-140, 1975) "the early development of vaccine for the control of BVD was done on the basis of the attenuation of the viral agent by serial passages in rabbits or in bovine kidney cell cultures. These vaccines proved effective in preventing BVD viral infections in cattle but there were reports of complications after vaccination". In the same paper, the authors also described the development of a porcine cell line attenuated BVD live virus vaccine "that will protect animals from virulent BVD viral infection and cause minimal stress to the animals".

Nevertheless the available live BVD vaccines do not avoid the other inherent hazards of the previously known ones (TERPSTRA, C., EIKELENBOOM, J. L. and GLAS, C, Proceedings of the XIIth world congress on diseases of cattle, vol. 1:177, 1982).

Several plausible reasons, other than the virulence of the vaccinal strain itself, have been postulated in an attempt to explain the severe postvaccinal complications occurring with variable frequencies in the field; nevertheless, their origin is difficult to assess and the vaccines have been questioned severely.

The present invention circumvents the hazards of BVD live vaccines known to date by providing modified strains which are temperature-sensitive (ts) mutant strains of the BVD virus, i.e. strains which show a replication ability considerably limited at the animal body temperature and which are capable of inducing immunity in bovines without serious side effects.

The modified strains of the present invention are prepared by mutagenesis of BVD virus strains, more particularly by treatment of a BVD virus strain with a chemical mutagen such as nitrous acid treatment of a BVD virus isolated from an infected animal, e.g. a BVD wild type strain isolated and deposited in accordance with the regulations of the European Patent Convention (EPC) in the "Collection Nationale de Cultures de Microorganismes" of the "Institut Pasteur" in Paris on July 20, 1982 under accession number I-198.

Mutagenesis by chemical agents is a technique known in the art and chemical agents known to induce mutagenesis and which can be used in the process of this invention are for instance, besides nitrous acid cited above, N-methyl-N-nitroso-N-nitro guanidine, methyl methane sulfonate, ethyl methane sulfonate, 5-bromo uracyl, 2-amino purine, hydroxylamine and acridine dyes such as 5-amino acridine and proflavine. More particularly, U.S. Pat. Nos. 3,907,986 and 3,962,424 describe the preparation of temperature-sensitive virus mutants by nitrous acid treatment and the use of said mutants in the preparation of live virus vaccines useful in the prevention of respiratory diseases in cattle. Nevertheless, temperature sensitive mutants of BVD virus were not known before this invention.

According to this invention, in order to prepare a vaccine strain from a wild type BVD virus strain, the strain is allowed to react with the chemical mutagen—e.g. nitrous acid—in operative conditions which reduce the initial virus titer by 2 to 3 $\log_{10}$ and, by culture of the resulting mutants at 35° C. and 39.5° C. respectively, a temperature sensitive (ts) mutant is then isolated showing at 39.5° C. (which is the temperature of the internal organs of bovines) a growth capacity which is about 3 $\log_{10}$ less than its growth capacity at 35° C. The temperature-sensitive mutant strain is isolated by being cloned in any tissue culture known to the art for accepting growth of bovine viral diarrhoea virus (for instance either the bovine kidney cell line which is on deposit, without restriction availability in the American Type Culture Collection under accession number ATCC CC144 or a bovine turbinate cells monolayer as described by McCLURKIN A. W. et al. in Arch. Gesam. Virusforsch. 45:285–289, 1974) at an appropriate dilution to allow selection of clones by end point dilution.

More particularly, a wild type strain isolated from an animal presenting typical symptoms of the bovine viral diarrhoea—e.g. the C.N.C.M. I-198 virus strain—is allowed to multiply in a tissue culture allowing growth of bovine diarrhoea virus—e.g. a cell line such as a bovine kidney cell line or a bovine turbinate cell line—eventually after adaptation of the strain to said tissue culture and a suspension of said bovine diarrhoea virus is allowed to react at room temperature with a chemical mutagen, for instance a buffered aqueous solution of nitrous acid—e.g. nitrous acid in acetic buffer, the concentration of nitrous acid and acetate ion in the medium being 4N and N respectively for one to 15 minutes—e.g. 6 ($\pm 1$) minutes—at a pH comprised between 5 and 6—e.g. at pH 5.7 ($\pm 0.1$)—after which period the reaction is stopped, e.g. by pH adjustment to 7.5 ($\pm 0.5$) by dropwise addition of normal sodium hydroxide. The suspension is then preferably dialysed and diluted aliquots are allowed to grow in a tissue culture as indicated above. The positive cultures are then comparatively cultivated and titrated at 35° C. and 39.5° C., selecting a culture showing a difference of titers of about 3 $\log_{10}$ TCID$_{50}$ between both temperatures. Such a temperature sensitive mutant is then eventually multiplied in a tissue culture allowing growth of the virus as indicated above and cloned by at least one end point dilution passage in order to isolate the temperature sensitive mutant, e.g. the C.N.C.M. I-199 virus strain. The virus is combined with a carrier for parenteral administration.

A laboratory trial conducted in immunodepressed animals with a C.N.C.M. I-199 strain containing vaccine showed a strong evidence of a significant improvement of this vaccine according to the invention over the previously existing vaccines.

The low level of symptoms observed with the C.N.C.M. I-199 strain indeed sharply contrasts with the severe clinical picture described in studies where either virulent or "attenuated" BVD strains were used in immunodepressed animals. Results of studies with virulent strains have been published by SHOPE R. E. et al. in Can. J. Vomp. Med. 40:355–359, 1976 and results of studies with an "attenuated strain" have been published by BITTLE J. S. and HOUSE J. A., J.A.V.M.A. 163:878–879, 1973 in this animal model. In this latter case, Bittle treated two calves with dexamethasone for 11 days and noticed that the animals remained normal until vaccination with an "attenuated virus (C24V)" and then exhibited typical signs of mucosal disease accompanied by fever and leukopenia as soon as immunodepressive treatment was discontinued. One animal died 24 days after vaccination whereas the other one eventually recovered.

In the trial where a vaccine containing the C.N.C.M. I-199 strain of this invention was used in immunodepressed calves, no clinical signs typical of mucosal disease were observed except various degrees of diarrhoea which uneventfully subsided. However, the BVD virus was not reisolated from the vaccinees despite daily attempts at recovering virus during the period digestive problems were observed. The clinical findings were thus not associated with the presence of vaccine virus in the feces or in the oculonasal secretions of vaccinates. The symptoms observed were not associated with viremia either but one should not exclude that at least partially they could be linked with a lowered immune potential to commensals like coccidia or enteroviruses due to the combination of dexamethasone treatment and BVD infection. It is also noteworthy that emergence of genetically altered vaccine virus was not observed.

Moreover, contrasting with the previously known vaccines whose active ingredient are a temperature-sensitive mutant and which are administered at a cold site of the organism, the vaccines of this invention are not infective when administered by such a route and must be administered by the classical parenteral route, i.e. either subcutaneously or in the muscle of the animal, with the proviso that said parenteral administration be followed by a booster somewhat, e.g. a few weeks, later.

Preferably the dosage unit of a vaccine according to the invention does contain at least $10^{3.5}$ TCID$_{50}$ and preferably at least $10^4$ TCID$_{50}$ of modified virus and is administered in at least two successive dosage units. Laboratory trials performed with a combined vaccine containing a BVD modified virus obtained according to the process of this invention and another live respiratory virus vaccine for cattle administrable by parenteral route (i.e. a bovine respiratory syncytial (BRS) virus vaccine) revealed that the BVD modified virus does not interfere with—i.e. does not affect—the immunogenicity of the other vaccinal virus and therefore according to another embodiment, this invention relates to combined live virus vaccines for cattle comprising a temperature-sensitive BVD virus mutant as indicated above with another live virus vaccine for cattle administrable by parenteral route.

The invention is illustrated by the following examples which should not be construed as limiting its scope.

EXAMPLE 1

Mutagenesis and selection of mutant

A strain of bovine diarrhoea virus from the nasal mucosa of a calf presenting typical symptoms of the disease was adapted to calf testicle cells culture by 10 passages in said tissue culture and deposited in accordance with the regulations of the European Patent Convention (EPC) in the "Collection Nationale de Cultures de Microorganismes" (C.N.C.M.) of the Institut Pasteur in Paris on July 20, 1982 under accession number I-198.

The virus was then multiplied by 6 passages in a bovine kidney cell line herein referred to as $NLBK_4$ cell line, using a medium consisting of a 50/50 (v/v) mixture of Basal and Minimal Eagle's media supplemented with 0.25% (w/v) of bovine lactalbumine hydrolysate.

A 1.25 ml volume of virus suspension resulting from the $16^{th}$ passage and containing $10^{4.0}$ $TCID_{50}/0.1$ ml, was mixed with 1.25 ml of molar acetic acid/sodium acetate buffer and 1.25 ml of a 4 molar sodium nitrite aqueous solution. The final pH of the mixture was 5.7. The mixture was then allowed to react for six minutes at laboratory temperature, after which period the reaction was stopped by dropwise addition of normal sodium hydroxide up to pH 7.5 ($\pm 0.5$). The pH adjustment was followed by change in colour of the phenol red indicator present in the virus suspension.

The treated virus suspension was immediately dialysed for 5 hours at 5° C. ($\pm 1$) in phosphate buffer saline consisting of NaCl (8 g.); KCl (0.2 g.); $Na_2HPO_4$ (1.15 g.); $KH_2PO_4$ (0.2 g.) in distilled water (up to 800 ml.) mixed with a solution of $MgCl_2.6H_2O$ in 100 ml of distilled water and thereafter with a solution of $CaCl_2$ (0.1 g.) in 100 ml. of distilled water, the final solution being sterilized by filtration, the final pH being comprised between 7.2 and 7.4). After dialysis the virus suspension was stored in liquid nitrogen.

Infectivity titration tests were performed at 37° C. using four tubes per tenfold dilution. Residual infectivity of the obtained virus suspension was $10^{1.7}$ $TCID_{50}/0.1$ ml of the infectivity of the starting C.N.C.M. I-198 virus strain suspension. Aliquots (0.1 ml) of virus suspension diluted 1/9 in a 50/50 (v/v) mixture of Basal and Minimal Eagle's media supplemented with 0.25% (w/v) of bovine lactalbumine hydrolysate were inoculated into eighty cultures of $NLBK_4$ bovine kidney cell line which were then incubated at 37° C. for 5 days. Among the 80 tubes, 31 exhibited cytopathogenic effect due to virus multiplication.

Each of these latter was comparatively cultivated and titrated at 35° C. and 39.5° C. These temperatures of incubation were selected as permissive and restrictive respectively because the starting virus (C.N.C.M. I-198) grew equally well at both temperatures and was handicaped at 40° C. One of the isolates exhibited a difference in titers of 3.0 $\log_{10}$ $TCID_{50}$ (tissue culture infective dose in 50% of the culture) between 35° C. and 39.5° C., demonstrating its temperature sensitivity. It was enriched by a supplementary passage ($19^{th}$) in the same operative conditions as the preceding passages and then freeze dried.

The virus was then multiplied by two passages in bovine turbinates cell line, herein referred to as $NLBT_1$, using the same medium as indicated above and a stock of virus was prepared at passage 21.

From this stock of virus, a further cloning passage at a $10^{-4.5}$ dilution was performed in the same conditions, using 96 cultures among which eight were positive. One of them was enriched by one further passage (24th) in the same conditions constituting a seed lot which was freeze dried in glass vials containing each $10^{3.9}$ $TCID_{50}$ of virus. Samples of the clone have been deposited in accordance with the regulations of the Europeant Patent Convention (EPC) in the "Collection Nationale de Cultures de Microorganismes" (C.N.C.M.) of the Institut Pasteur in Paris on July 20, 1982 under accession number I-199.

EXAMPLE 2

Vaccine preparation

A sample of the seed lot (C.N.C.M. I-199) was rehydrated and inoculated in $NLBT_1$ cell cultures which were then covered with maintenance medium described above.

The cells were incubated at permissive temperature (35° C.$\pm 0.5$) 5 days. The supernatant was then freshly inoculated to another series of cultures. When the cytopathogenic effect appeared in 50% of the monolayers, the supernatants were harvested and pooled, casitone (6% w/v) was added thereto and the mixture was stored at $-70$° C. This virus suspension was thawed, distributed in glass vials and freeze dried to contain $10^4$ $TCID_{50}$ or multiples thereof per vial.

Before administration, the vaccine is extemporaneously rehydrated with saline (NaCl 0.9% in sterile distilled water) using 2.0 ml per dosis. The vaccine is administered by intramuscular route and, preferably, two doses are administered e.g. at a three week interval.

EXAMPLE 3

Temperature sensitivity of the modified strain

The efficiency of plaquing (EOP) expressed as $\log_{10}$ PFU (plaque forming units) per 0.2 ml after incubation at different temperatures has been determined for each of the strains C.N.C.M. I-198 and I-199. The results are indicated in Table 1 which shows that EOP is comprised between $10^{4.5}$ to $10^{5.0}$ for the wild strain C.N.C.M. I-198 whereas the mutant C.N.C.M. I-199 has an optimal EOP at 35°–37° C., which is reduced by 1.5 $\log_{10}$ at 39° C. and by 3.0 log at 39.5° C., no infectious virus being recovered from the inoculated cultures which are not positive for CPE at 39.5° C.

TABLE 1

| Strain | Efficiency of plaquing (EOP) at | | | | |
|---|---|---|---|---|---|
|  | 35° C. | 37° C. | 38.5° C. | 39° C. | 39.5° C. |
| CNCM I-198 | 4,8 | 4,8 | NT | NT | 4,8 |
| CNCM I-199 | 4,2 | 4,2 | 3,6 | 2,7 | 1,2 |

The titres at 35° C. and 39.5° C. were also determined for the virus at different passage levels and the results are given in Table 2 which shows that the difference between the titers at 35° C. and 39.5° C. is stable over the different passages levels of the virus.

TABLE 2

| | Comparative titers on $NLBT_1$ cell line at permissive and restrictive temperatures | | | |
|---|---|---|---|---|
| | | Number | Ratio 35°/39.5° C. (x) | |
| Virus | Passage level | of tests | Geometric mean | Standard deviation |
| CNCM I-198 | 17 | 17 | 0.2 | 0.1 |
| CNCM I-199 | 21 | 6 | 2.4 | 0.3 |
| | 23 | 2 | 2.1 | |
| | 24 | 15 | 3.0 | 0.4 |
| | 28 | 16 | 3.2 | 0.4 |

(x) $\frac{\log TCID_{50} \text{ or PFU at } 35° \text{ C.}}{\log TCID_{50} \text{ or PFU at } 39.5° \text{ C.}}$

EXAMPLE 4

Attenuation for normal calves

The seed lot of vaccine was tested in five seronegative animals. Therefore, ten vaccine doses were rehydrated in 2 ml of normal saline and inoculated by intramuscular route to each animal. A same dose of the vaccine was administered similarly three weeks later.

Clinical examination, rectal temperature records and white blood cell counts were performed daily for 14 days after the administration of the first dose.

No symptoms were observed. As can be seen in Table 3, no increase in body temperature above 39.2° C. was recorded.

TABLE 3

| Day | Rectal temperature records (in °C.) Calf No | | | | |
|---|---|---|---|---|---|
| (x) | 010 | 012 | 431 | 432 | 433 |
| −10 | 38.2 | 38.5 | 38.5 | 38.7 | 38.6 |
| −9 | 38.0 | 38.0 | 38.5 | 38.7 | 38.6 |
| −8 | 38.1 | 37.8 | 38.8 | 38.7 | 39.2 |
| −7 | 38.0 | 38.0 | 39.0 | 38.8 | 38.7 |
| −3 | 38.2 | 38.0 | 38.8 | 39.0 | 38.7 |
| −2 | 38.0 | 38.2 | 39.0 | 38.9 | 38.7 |
| −1 | 38.5 | 38.2 | 38.2 | 38.6 | 38.0 |
| 0 | 38.3 | 38.0 | 39.0 | 38.9 | 38.7 |
| 1 | 38.4 | 38.0 | 38.7 | 38.9 | 38.8 |
| 5 | 38.3 | 38.3 | 38.9 | 38.6 | 38.6 |
| 6 | 38.0 | 38.2 | 38.8 | 38.6 | 38.6 |
| 7 | 38.2 | 38.2 | 38.5 | 38.8 | 38.4 |
| 8 | 38.4 | 38.6 | 39.0 | 38.7 | 38.5 |
| 11 | 38.2 | 38.4 | 38.8 | 38.5 | 38.5 |
| 12 | 38.4 | 38.4 | 38.8 | 38.5 | 38.0 |
| 13 | 38.4 | 38.2 | 38.4 | 38.4 | 38.4 |
| 14 | 38.6 | 38.1 | 38.8 | 39.0 | 38.7 |

(x) day 0 is inoculation of the first dose.

The average number of white blood cells (WBC) count remained normal throughout the observation period.

As demonstrated by their seroconversion against BVD, all animals were immunized.

EXAMPLE 5

Attenuation for immunodepressed animals

Nine calves seronegative to both BVD and bovine respiratory syncytial (BRS) viruses were treated daily with dexamethasone 0.1 mg/kg during a period of 12 consecutive days beginning on day 5 before the administration of the first dose of vaccine.

Four animals (Nos 16, 30, 82 and 83) were inoculated intramuscularly with the seed lot on day 0 and received similarly an identical dose on day 21. The vaccination on day 0 is herein referred to as first vaccination and the dose of vaccine used for the first vaccination was $10^5$ TCID$_{50}$ of the vaccine obtained in example 2.

On day 0 and 21 three animals (i.e. Nos 13, 14 and 19) were vaccinated with a combined BRS/BVD virus vaccine containing $10^{5.7}$ TCID$_{50}$ of BRS virus and $10^5$ TCID$_{50}$ of BVD virus. Two animals (i.e. Nos 80 and 81) were vaccinated on days 0 and 21 only and with the same BRS virus vaccine containing $10^{5.7}$ TCID$_{50}$ of virus per dose.

Clinical examination, body temperature records and WBC counts were performed for 14 days after the first dose. Virus isolation was attempted daily on blood samples, oculonasal swabs and fecal material of four of the inoculated calves during the same period. The results and their interpretation are given in Tables 4 and 5.

TABLE 4

| CALF NO. | CLINICAL SCORES DAILY SCORES (days after 1st vaccination) | | | | | | | | | | | | | | | | | AVERAGES | |
|---|---|---|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15// | 21 | INDIVID. | GROUP |
| 30 | − | − | − | − | − | − | 80 | 70 | 70 | 30 | − | − | − | − | − | − | − | 11,9 | 15,25 |
| 83 | − | − | − | 30 | 30 | 30 | 50 | 50 | 40 | 40 | 40 | 10 | 10 | 10 | 10 | − | − | 16,7 | |
| 82 | − | − | − | − | − | − | 50 | 50 | 50 | 60 | 50 | 50 | 50 | 50 | 20 | − | − | 20,5 | |
| 16 | − | 20 | 20 | 20 | 20 | 20 | 30 | 30 | 30 | 30 | 20 | 10 | 10 | 30 | 10 | − | − | 11,9 | |
| DAILY AVERAGE | | 5 | 12,5 | 12,5 | 12,5 | 12,5 | 52,5 | 50,0 | 47,5 | 40,0 | 27,5 | 17,5 | 17,5 | 22,5 | 10,0 | − | − | | |
| 19 | − | − | − | − | − | − | 20 | − | − | 30 | − | − | − | − | − | − | − | 2,4 | 15,20 |
| 13 | − | − | − | 30 | 30 | 30 | 60 | 60 | 60 | 60 | 60 | 10 | 10 | − | − | − | − | 19,5 | |
| 14 | − | − | 30 | 30 | 30 | 30 | 50 | 50 | 80 | 60 | 60 | 30 | 30 | 10 | 10 | − | − | 23,8 | |
| DAILY AVERAGE | | | 7,5 | 15,0 | 15,0 | 15,0 | 40,0 | 35,0 | 35,0 | 37,5 | 30,0 | 10,0 | 10,0 | 2,5 | 2,5 | − | − | | |
| 80 | − | − | − | − | − | − | − | − | − | − | − | − | − | − | − | − | − | 0 | 2,15 |
| 81 | − | − | − | − | − | − | 30 | 30 | 30 | − | − | − | − | − | − | − | − | 4,3 | |
| DAILY AVERAGE | | | | | | | 15,0 | 15,0 | 15,0 | | | | | | | | | | |

−: negative

TABLE 5

| METHOD OF CALCULATION OF CLINICAL SCORES | | | | |
|---|---|---|---|---|
| Parameter | Degree | Score Unit (1) | Score weighting (2) | Clinical score |
| Apathy | none | 0 | 10 | Sum of (1) multiplied by (2) |
| | slight | 1 | | |
| | decubitus | 2 | | |
| Anorexia | none | 0 | 20 | |
| | reduced appetite | 1 | | |
| | complete | 2 | | |
| Diarrhoea | normal feces | 0 | 10 | |
| | soft feces | 1 | | |
| | aqueous feces | 2 | | |
| | moelena | 3 | | |
| | necrosis | 4 | | |

It appears that various degrees of anorexia and diarrhoea were observed in all vaccinated calves. However none of them had either hyperthermia or leukopenia and no BVD virus was reisolated from the samples collected. No cumulative pathogenicity due to the combination of BRS and BVD or interference was observed.

EXAMPLE 6

Efficacy of the C.N.C.M. strain I-199 against an artificial challenge

The animals vaccinated during immunodepressive treatment seroconverted after administration of the second dose. They were, as well as the two controls (animals vaccinated with BRS only), challenged on day 35 after administration of the first dose.

The BVD virus used for the challenge was the Osloss strain (ROHDE G. and LIESS B., Zbl. Vet. Med. 17 B:686, 1970). It was administered intranasally using $10^{6.8}$ TCID$_{50}$ per animal.

Clinical symptoms, body temperature, white blood cell counts were performed for 14 days after challenge. Virus reisolation was attempted from the blood of all the animals.

No clinical symptom nor hyperthermia were observed.

Calves that had received two doses of the vaccine had no decrease in WBC count after challenge whereas the controls (animals Nos 80 and 81) were leukopenic.

Even at the high dose of $10^{6.8}$ TCID$_{50}$/animal, the Osloss strain was not pathogenic. Neither hyperthermia nor clinical symptoms were observed in control animals nos. 80 and 81 which had been vaccinated with the BRS virus vaccine only. However, these two animals had lower WBC counts than the calves which received two doses of BVD vaccine and viremia was evidenced in those calves. Animals vaccinated with the BVD/BRS combined vaccine were equally well protected (Nos 19, 13 and 14).

The results are summarized in Table 6.

TABLE 6

| Calf NO. | Vaccine | Viraemia after challenge Day post inoculation | | | | | | | | | | Index |
|---|---|---|---|---|---|---|---|---|---|---|---|---|
| | | 0 | 2 | 4 | 5 | 6 | 7 | 8 | 9 | 10 | 13 | |
| 16 | BVD | − | − | − | − | − | − | − | − | − | − | 2/68 |
| 30 | | − | − | − | − | − | − | − | − | − | − | |
| 82 | | − | − | − | − | − | + | − | + | − | − | |
| 83 | | − | − | − | − | − | − | − | − | − | − | |
| 13 | BVD/ | − | − | − | − | − | NT | − | − | − | − | |
| 14 | BSR | − | − | − | − | − | NT | − | − | − | − | |
| 19 | | − | − | − | − | − | − | − | − | − | − | |
| 80 | BRS | − | − | + | + | + | + | + | − | − | − | 9/20 |
| 81 | | − | − | − | + | + | + | + | − | − | − | |

− IF (Immunofluorescence test) negative
+ IF (Immunofluorescence test) postive
NT not tested These results do not contrast with those of the literature since it is known that experimental infection with wild type BVD seldom results in severe clinical symptoms (SAURAT P. et al., La Maladie des Muqueuses, Ed. L'Expansion Scientifique Francaise, Paris 1972, p. 76).

The index, (i.e. number of positive samples as a proportion of the number of samples tested, was significantly higher (9/20) for the group of animals vaccinated with BRS only than for the other calves among which two calves were transiently positive.

EXAMPLE 7

Efficacy of the C.N.C.M. I-199 strain in the field

One hundred and three calves aged 15 days to 18 months having low (i.e. $\leq 8$) antibody titers against BVD were administered by intramuscular route two doses of $10^{4.0}$ TCID$_{50}$ of the vaccine of Example 2, three weeks apart. No clinical reaction attributable to the vaccine were reported, demonstrating the safety of the vaccine in field conditions.

The results are summarized in Table 7.

TABLE 7

| Antibody titer before vaccination | Number of seroconverting/Total number of animals | | | | | | |
|---|---|---|---|---|---|---|---|
| | <1 | | | 1-8 | | | Total |
| Age (+) | $\leq 2$ | >2 | Total | $\leq 2$ | >2 | Total | Total |
| Total numbers | 9/20 | 51/57 | 60/77 | 2/6 | 6/10 | 8/16 | 68/9 |
| Percents | 45 | 90 | 78 | 30 | 60 | 50 | 73 |

(+) in months

As can be seen from Table 7, overall, 73% of the animals had a significant antibody increase after vaccination. However, considering only the calves which were seronegative at vaccination, there was a clear difference (p<0.001) in the seroconversion rate of the animals older than two months (90%) compared to the younger ones (45%). The seropositive animals show the same trend. A better response of older animals was observed.

In seronegative animals more than two months old, the temperature-sensitive strain C.N.C.M. I-199 induced 90% of seroconversion after two doses of $10^4$ TCID$_{50}$. This observation does not contrast with the rate of 95 to 98% obtained in the optimal conditions with commercially available vaccines (LAMBERT G. et al., Modern Vet. Practice p. 34, April 1970). The seroconversion rate of 50%, observed in calves less than two months old, is in agreement with the results obtained by SMITH P. E. et al. (Vet. Med. Small Anim. 63:457, 1968), who reported a positive response to vaccination in 5/10 animals under 60 days of age and in 42/48 older animals having a similar immunological status at vaccination. In the present trial, sixteen seropositive animals having low maternal antibody titers were vaccinated and 50% seroconverted. Although the numbers are small, these results indicate that successful immunization can be achieved in animals over 2 months of age having low antibody titers at vaccination.

We claim:

1. A live bovine viral diarrhoea (BVD) virus vaccine capable of inducing immunity in bovines comprising an effective amount to induce immunity of at least $10^{3.5}$ TCID$_{50}$ of a temperature sensitive (ts) mutant of BVD virus wherein the ts mutant is obtained by mutagenesis with nitrous acid and wherein the mutant shows a replication ability considerably limited at the animal body temperature, 39.5° C., and shows a difference of infectious titer of about 3 log 10 TCID$_{50}$ between 35° C. and 39.5° C.

2. A vaccine according to claim 1 wherein the mutagenesis is performed by bringing a BVD virus strain into contact with nitrous acid in a buffered aqueous medium at a pH between 5 and 6 for one to 15 minutes.

3. A vaccine according to claim 1 or 2 further comprising at least one live bovine respiratory virus vaccine.

4. A method of protecting a bovine against respiratory viral diseases including bovine viral diarrhoea disease which comprises administering by parenteral route to said bovine at least two successive dosage units of a vaccine according to claim 3.

5. A vaccine according to claim 1 or 2 further comprising live bovine respiratory syncytial (BRS) virus vaccine.

6. A method of protecting a bovine against bovine viral diarrhoea disease and against the disease provoked by respiratory syncytial virus which comprises administering by parenteral route to said bovine at least two successive dosage units of a vaccine according to claim 5.

7. A vaccine according to claim 1 or 2 wherein the ts mutant is the BVD virus strain C.N.C.M. I-199.

8. A method of protecting a bovine against bovine viral diarrhoea disease which comprises administering by parenteral route to said bovine at least two successive dosage units of the vaccine of claim 7.

9. A method of protecting a bovine against bovine viral diarrhoea disease which comprises administering by parenteral route to said bovine at least two successive dosage units of a vaccine according to claim 1 or 2.

10. A process, for preparing a temperature sensitive strain of bovine viral diarrhoea (BVD) virus which comprises bringing a BVD virus strain into contact at room temperature with nitrous acid under conditions of nitrous acid concentration, pH and time, to reduce the initial virus titer by 2 to 3 $\log_{10}$ and after growth in tissue culture, isolating a temperature sensitive mutant showing a difference of titer of about 3 $\log_{10}$ TCID$_{50}$ between 35° and 39.5° C.

11. A process according to claim 10 wherein the BVD virus strain is brought into contact with nitrous acid in a buffered aqueous medium at a pH between 5 and 6 for one to 15 minutes.

12. A process according to claim 11 wherein the reaction period is 6 minutes ($\pm 1$), the pH is 5.7 ($\pm 0.1$) and the reaction medium is 4N nitrous acid in normal acetic acid/acetate buffer.

13. A process according to claim 12 wherein the isolated temperature sensitive mutant is the strain C.N.C.M. I-199.

14. A process for preparing a bovine viral diarrhoea (BVD) virus vaccine comprising growing in a suitable cell culture the temperature sensitive mutant isolated by the process of claim 11 to permit growth of a greater amount of said mutant and combining the modified virus with a carrier for parenteral administration.

15. A process according to claim 14 wherein said temperature sensitive mutant is the C.N.C.M. I-199 strain.

16. A process according to claim 14 or 15 wherein the temperature sensitive combined with a live bovine respiratory virus vaccine.

17. A process according to claim 16 wherein the live bovine respiratory virus vaccine is a live bovine respiratory syncytial (BRS) virus vaccine.

* * * * *